United States Patent [19]

Saito et al.

[11] Patent Number: 5,174,294

[45] Date of Patent: Dec. 29, 1992

[54] SHOCKWAVE TREATMENT APPARATUS

[75] Inventors: Koji Saito; Nobuki Kudo, both of Tochigi, Japan

[73] Assignee: Kabushiki Kaisha Toshiba, Kawasaki, Japan

[21] Appl. No.: 855,466

[22] Filed: Mar. 23, 1992

Related U.S. Application Data

[63] Continuation of Ser. No. 426,542, Oct. 26, 1989, abandoned.

[30] Foreign Application Priority Data

Oct. 26, 1988 [JP] Japan .................. 63-271456
Oct. 31, 1988 [JP] Japan .................. 63-276637

[51] Int. Cl.⁵ .......................................... A61B 17/22
[52] U.S. Cl. ..................... 128/660.05; 128/24 EL; 128/660.03
[58] Field of Search ........ 128/24 AA, 24 EL, 660.03, 128/660.05, 661.07, 661.08, 661.09, 662.01, 662.04

[56] References Cited

U.S. PATENT DOCUMENTS

| | | | |
|---|---|---|---|
| 4,313,444 | 2/1982 | Glenn | 128/660.05 |
| 4,612,937 | 9/1986 | Miller . | |
| 4,622,978 | 11/1986 | Matsuo et al. . | |
| 4,787,394 | 11/1988 | Ogura | 128/660.03 |
| 4,787,395 | 11/1988 | Yanashima et al. | 128/661.09 |
| 4,803,995 | 2/1989 | Ishida et al. | 128/660.03 |
| 4,817,617 | 4/1989 | Takeuchi et al. | 128/660.05 |
| 4,867,167 | 9/1989 | Magnin | 128/661.07 |
| 4,918,605 | 4/1990 | Shiroska | 128/661.09 |
| 4,923,414 | 6/1990 | Coleman et al. | 128/660.03 |
| 4,930,514 | 6/1990 | Baba et al. | 128/661.09 |
| 4,942,878 | 7/1990 | Dory | 128/660.03 |
| 5,005,579 | 4/1991 | Wurster et al. | 128/660.03 |
| 5,040,537 | 8/1991 | Katakura | 128/24 AA |

FOREIGN PATENT DOCUMENTS

| | | |
|---|---|---|
| 0019793A2 | 5/1980 | European Pat. Off. . |
| 0190979A2 | 2/1986 | European Pat. Off. . |
| 3119295A1 | 12/1982 | Fed. Rep. of Germany . |
| 3743883A1 | 7/1988 | Fed. Rep. of Germany . |
| WO8701927 | 4/1987 | PCT Int'l Appl. . |

Primary Examiner—Lee S. Cohen
Assistant Examiner—Krista M. Pfaffle
Attorney, Agent, or Firm—Finnegan, Henderson, Farabow, Garrett and Dunner

[57] ABSTRACT

A shock wave treatment apparatus, in which a shock wave generator generates a shock wave toward a living body having an object to be disintegrated by the shock wave, and an ultrasonic wave probe transmits an ultrasonic wave toward the living body and receives an ultrasonic wave echo from the living body, in which a B-mode processor forms a B-mode section image from the ultrasonic wave echo, and a color flow mapping processor forms a color flow mapping image from the ultrasonic wave echo, and in which the B-mode section image and the color flow mapping image are displayed on a display. A processor for obtaining doppler information from the ultrasonic wave echo to reproduce doppler sounds from the doppler information may be also provided.

12 Claims, 9 Drawing Sheets

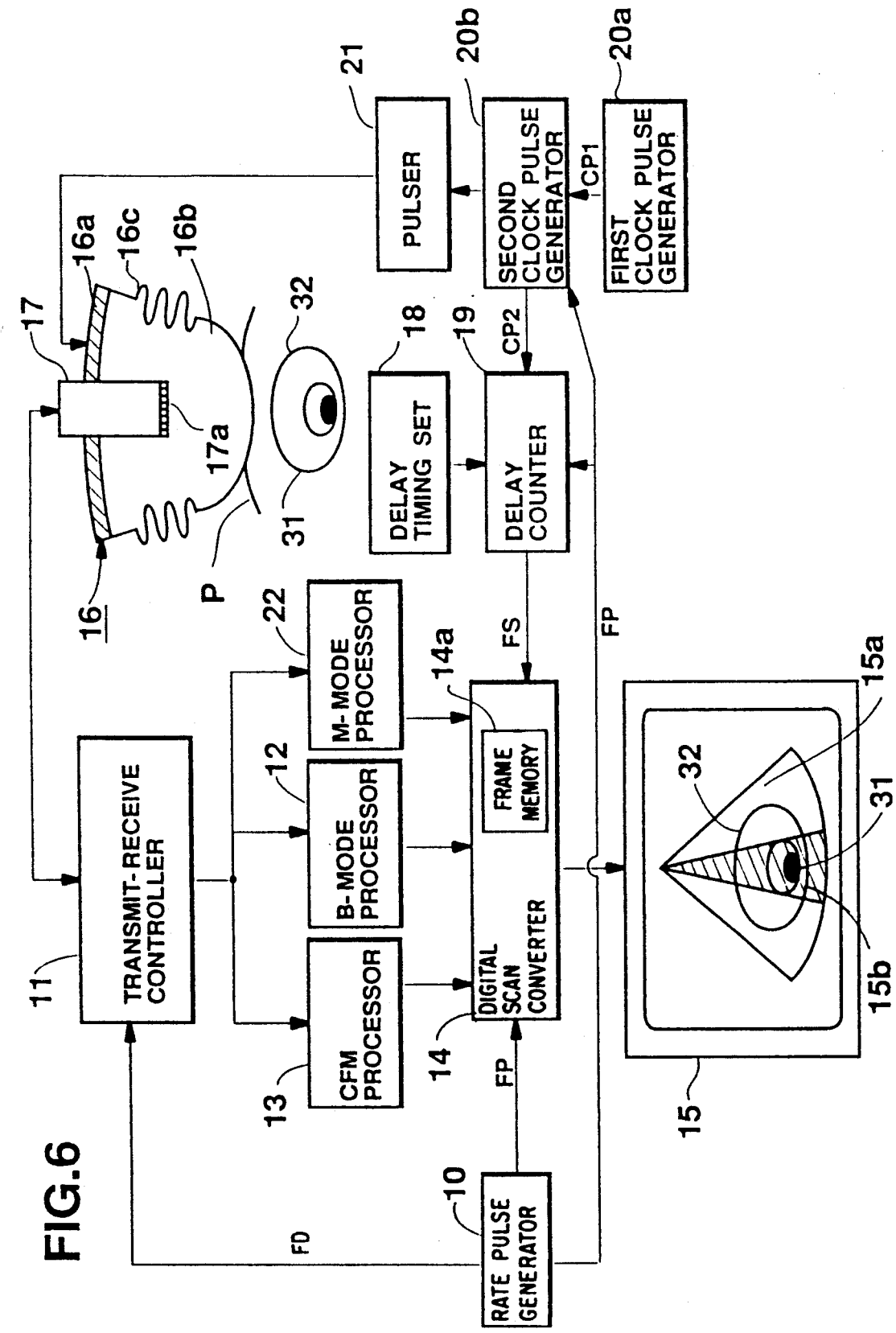

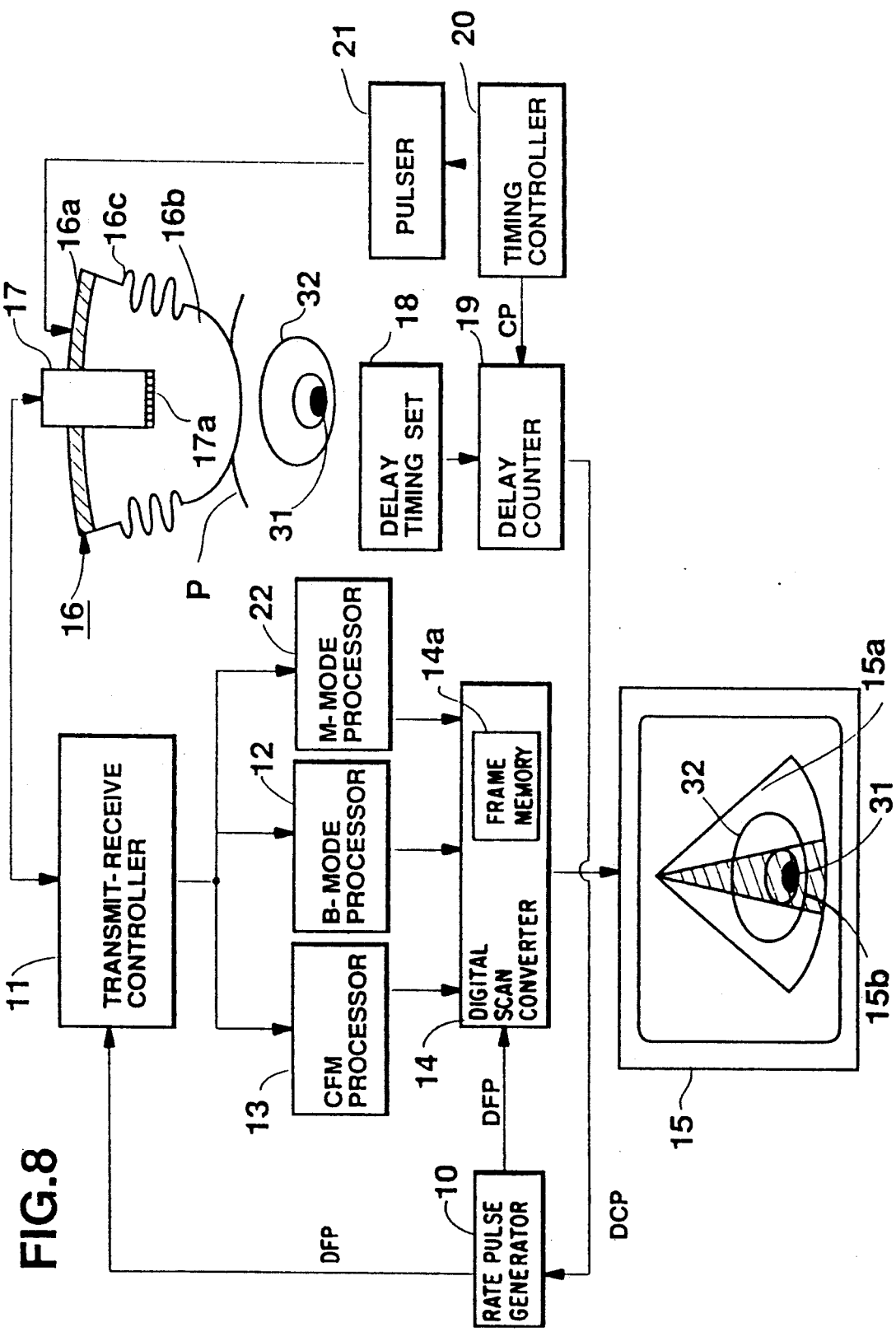

SHOCKWAVE TREATMENT APPARATUS

This application is a continuation of application Ser. No. 07/426,542 filed Oct. 26, 1989, now abandoned.

BACKGROUND OF THE INVENTION

1. Field of the Invention

The present invention relates to a shock wave treatment apparatus for a treatment such as disintegration of an object such as a cancer, a concretion or the like present within a living body by concentrating shock waves on the object located in a focal region or point.

2. Description of the Background Art

In FIG. 1, there is shown a conventional shock wave generator 1 for destruction or disintegration of a concretion or the like within a living body, as disclosed in Japanese Patent Laid-Open Specification No. 62-49843. In this shock wave generator 1, a shock wave transducer 2 having a spherical concave front surface of a certain curvature includes a central through hole 2a of a certain shape, and the transducer 2 is supported by a backing member 3 adhered to the back surface of the transducer 2. A ultrasonic wave probe 4 for scanning the living body to obtain a B-mode section image or the like is provided with an ultrasonic wave transmitting-receiving surface or alley 4a in its one end, and the alley 4a is positioned at the same curved plane of the spherical surface of the transducer 2 or retracted therefrom so as to be positioned behind the curved plane. The shock wave generator 1 applies shock waves to a living body 6 via a water bag 5 containing water therein.

When a concretion within a living body is to be disintegrated using the above described shock wave generator 1, a concentration point positioning procedure must be performed. That is, the concentration point of the shock waves generated by the transducer 2 must be adjusted such that it coincides with the concretion. This concentration point positioning procedure is effected by displaying a B-mode section image of the living body including the concretion and a target mark representing the concentration point of the shock waves on the display and by adjusting the target mark to coincide with the, B-mode image of the concretion on the display. In this case, the target mark is geometrically determined depending on the ultrasonic wave generator 1.

However, in this case, in practice, it is not easy to confirm the position of the concretion in the B-mode image on the display and the actual concentration point of the shock waves generated by the tranducer is often somewhat different or shifted from the position represented by the target mark. Therefore the actual concentration point of the shock waves can not be confirmed. Further, after the generation of the shock waves to the concretion, it is difficult to confirm how much of the concretion has been disintegrated.

SUMMARY OF THE INVENTION

It is therefore an object of the present invention to provide a shock wave treatment apparatus free from the aforementioned defects and disadvantages of the prior art, which is capable of readily confirming a position of an object to be disintegrated and an actual concentration point of shock waves generated by a shock wave transducer, and confirming results of the shock wave generation to the object.

In accordance with one aspect of the present invention, there is provided a shock wave treatment apparatus, comprising means for generating a shock wave toward a living body having an object to be disintegrated by the shock wave, an ultrasonic wave probe for transmitting an ultrasonic wave toward the living body or receiving an ultrasonic wave echo from the living body, means for forming a B-mode section image of the living body on the basis of the ultrasonic wave echo, means for obtaining an ultrasonic wave doppler alteration frequency from the ultrasonic wave echo and for performing a color flow mapping process on the basis of the ultrasonic wave doppler alteration frequency to form a color flow mapping image of the living body, and means for displaying at least one of the B-mode section image and the color flow mapping image.

In accordance with another aspect of the present invention, there is provided a shock wave treatment apparatus, comprising means for generating a shock wave toward a living body having an object to be disintegrated by the shock wave, an ultrasonic wave probe for transmitting an ultrasonic wave toward the living body or receiving an ultrasonic wave echo from the living body, means for performing a phase detection of the ultrasonic wave echo to obtain doppler information, and means for reproducing sound from the doppler information.

BRIEF DESCRIPTION OF THE DRAWINGS

The above and other objects, features and advantages of the present invention will more fully appear from the following description of the preferred embodiments with reference to the accompanying drawings, in which:

FIG. 6 is a block diagram of a second embodiment of a shock wave treatment apparatus according to the present invention;

FIG. 8 is a block diagram of a third embodiment of a shock wave treatment apparatus according to the present invention;

DESCRIPTION OF THE PREFERRED EMBODIMENTS

Figure 2:
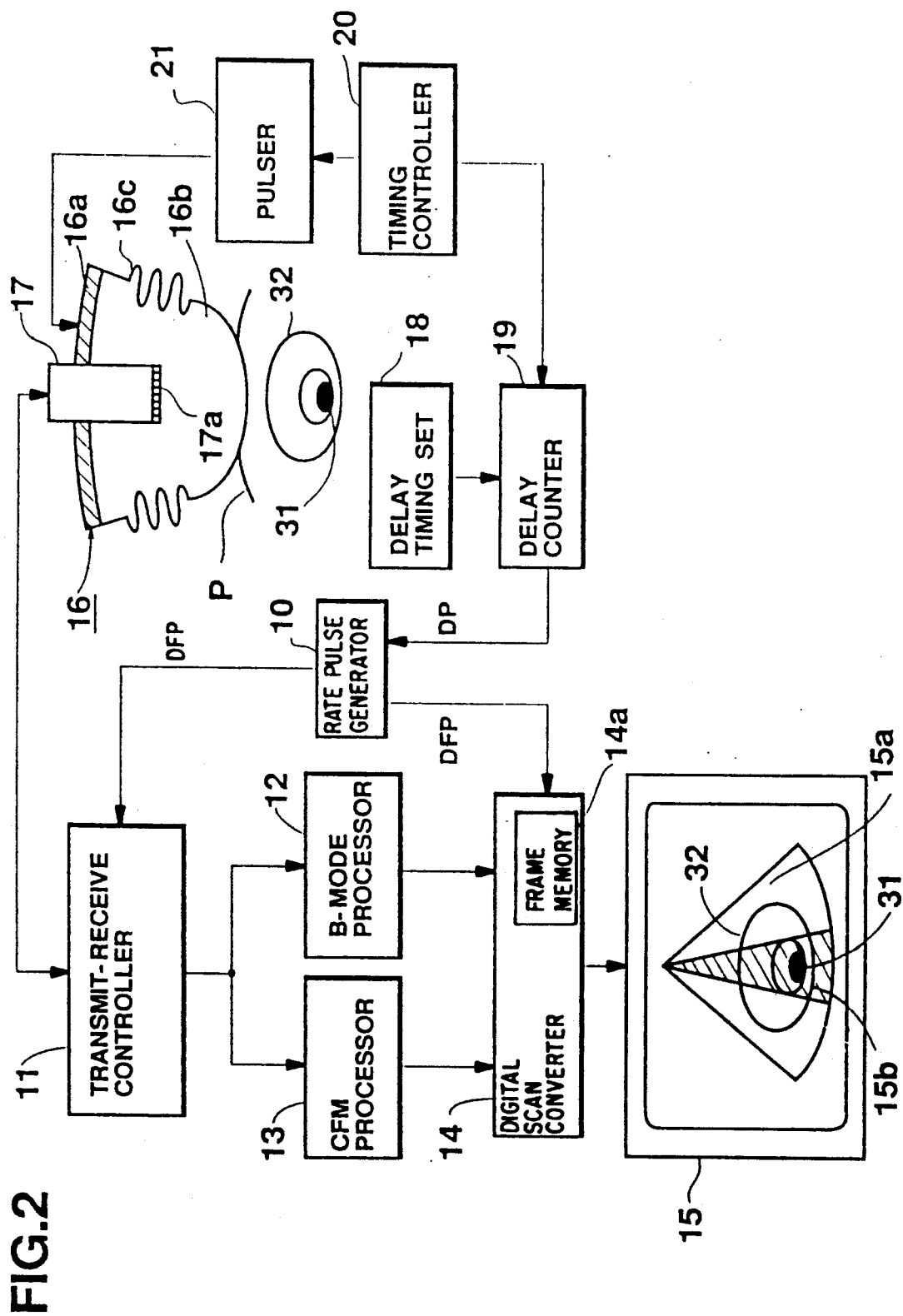
FIG. 2 is a block diagram of a first embodiment of a shock wave treatment apparatus according to the present invention.

Referring now to the drawings, wherein like reference characters designate like or corresponding members throughout the several views and thus the repeated description thereof may be omitted for brevity, there is shown in FIG. 2 a first embodiment of a shock wave treatment apparatus according to the present invention.

In FIG. 2, a shock wave generator 16 includes a shock wave transducer 16a having a spherical concave surface for generating shock waves therefrom and a water bag 16b having flexible bellows 16c for performing an effective transmission of the shock waves to a living body P, for instance, in order to disintegrate a concretion 31 of an object 32 such as a kidney or the like. The shock wave transducer 16a is formed with a central hole therein. In this embodiment, various devices such as a vibrator having a concave semisphere form, an electromagnetic induction type sound source including a combination of a spiral coil and a metal membrane arranged close thereto, and the like, can be used to provide the shock wave transducer 16a. An ultrasonic wave probe 17 having a ultrasonic wave transmitting-receiving surface or alley 17a in its end is arranged in the central hole portion of the shock wave transducer 16a. The ultrasonic wave probe 17 transmits an ultrasonic wave toward the living body P and receives an ultrasonic wave echo therefrom to effect a scanning of the living body P for obtaining a B-mode section image, a CFM (color flow mapping) image and an M-mode image.

A timing controller 20 outputs a shock wave generation timing signal to a delay counter 19 and a pulser 21. The pulser 21 sends a drive signal to the shock wave transducer 16a in order to drive the same, and its driving timing is controlled by the shock wave generation timing signal fed from the timing controller 20. The delay counter 19 outputs a delayed pulse DP to an RPG (rate pulse generator) the delay pulse DP timing being delayed by a certain period of time after the shock wave generation timing. The delay timing of the delayed pulse DP output by the delay counter 19 is controlled by a delay timing set 18.

The RPC 10 generates a delayed frame pulse DFP to a transmit-receive controller 11 and a DSC (digital scan converter) 14 in synchronization with the delayed pulse DP output from the delay counter 19. The transmit-receive controller 11 controls the ultrasonic wave probe 17 to transmit or receive the ultrasonic wave to or from the living body P. The transmit-receive controller 11 comprises a transmitter and a receiver. The transmitter includes a transmission delay device for setting a certain delay time for the transmission of the delayed frame pulse and a pulser for generating a pulse for driving the alley 17a of the ultrasonic wave probe 17 in synchronization with the delay time given by the transmission delay device. The receiver includes a preamplifier for amplifying a ultrasonic wave echo received by the ultrasonic wave probe 17, a receipt delay device for setting a certain delay time for the output of the amplified ultrasonic wave echo, and an adder for adding the delayed echoes.

A B-mode processor 12 includes a detector for performing an amplitude detection of an output addition signal of the transmit-receive controller 11, and an A/D (analog-digital) converter for converting the amplitude detected signal to a digital detected signal to obtain a monochrome B-mode section image. The operated results of the B-mode processor 12 are sent to the DSC 14. A CFM (color flow mapping) processor 13 includes a phase detector for effecting a phase detection of the ultrasonic wave echo, an MTI (moving target indication) filter for removing a clutter component of the output signal of the phase detector, an auto correlator for performing an auto correlation of the output signal of the MTI to obtain an ultrasonic wave doppler alteration frequency, and a processor for operating an average speed and a power of a moving object according to the ultrasonic wave doppler alteration frequency to obtain a CFM (color flow mapping) image. That is, the CFM processor 13 performs the color flow mapping process to obtain a CFM image. The obtained result of the CFM processor 13 is fed to the DSC 14.

The DSC 14 is provided with a frame memory (FM) 14a, in which the scan conversion between the sampling and display systems is carried out. The writing timing of the data into the FM 14a of the DSC 14 is determined by the delayed frame pulse DFP output from the RPG 10. The data of the B-mode section image and the CFM image is stored in the FM 14a of the DSC 14. The scan conversion result in the DSC 14 is fed to a color display 15. On the color display 15, the monochrome B-mode section image 15a and the CFM image 15b overlapped thereon are reproduced.

Figure 1:
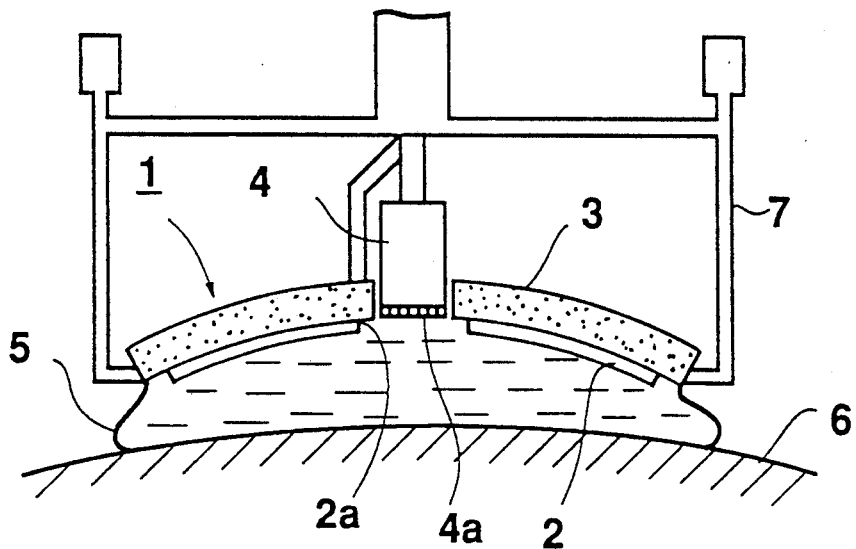
FIG. 1 is a longitudinal cross sectional view of a conventional shock wave generator.
Figure 3:
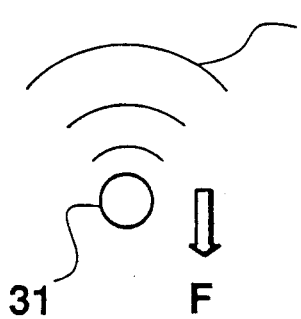
FIGS. 3 to 5 are schematic views of an object to be disintegrated by giving shock waves generated by a transducer according to the present invention.
Figure 4:
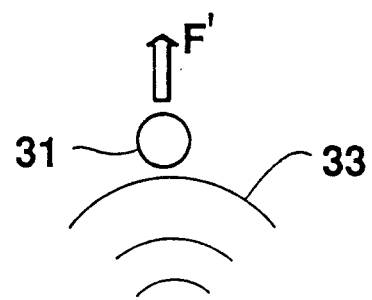

When the shock waves are generated by the shock wave transducer 16a, a large pressure such as several 100 to 1000 bar is exerted at the concentration point. As shown in FIG. 3, soon after the shock wave 33 traveling in a direction F hits an object 31 such as a concretion to be disintegrated, the object 31 receives a large pressure and is moved in the direction F. Then, after the shock wave 33 passes through the object 31, the object 31 is pulled back in a direction F' opposite the direction F by a negative pressure component created as the shock wave 33 travels in the direction F', as shown in FIG. 4. Thus, the object 31 performs damped oscillation.

Figure 5:
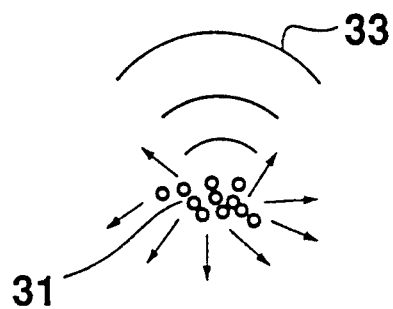

When the object 31 is not disintegrated by the shock wave 33, the object 31 performs damped oscillation while the object 31 retains its original form. However, when the object is disintegrated by the shock wave 33, as shown in FIG. 5, the disintegrated pieces of the object are moved in all directions depending on their relative positions with respect to the concentration point of the shock wave and the surrounding conditions thereof. Hence, the behavior of the disintegrated pieces can be observed by transmitting an ultrasonic wave to a certain region containing the disintegrated pieces, obtaining frequency alteration information of the ultrasonic wave and analyzing the obtained frequency alteration information.

According to the present invention, an ultrasonic wave doppler alteration frequency of an ultrasonic wave is obtained from a received ultrasonic wave echo, and a CFM (color flow mapping) process is effected on the basis of the ultrasonic wave doppler alteration frequency. The result of the CFM process is overlapped on a B-mode section image on a display, and this is used as a monitory image during a shock wave treatment, as hereinafter described in detail.

The operation of the above described apparatus will now be described in detail.

The ultrasonic wave probe 17 effects the transmission and receipt of the ultrasonic wave to and from the living body P by the transmit-receive controller 11, and the transmit-receive controller 11 obtains the ultrasonic wave echo. The B-mode processor 12 outputs the result of the B-mode process to the DSC 14, and the B-mode section image 15a of the living body P is stored in the FM 14a of the DSC 14. Then, the data of the B-mode section image 15a is read out of the FM 14a and is sent to the display 15 to display the B-mode section image 15a thereon.

When the shock wave transducer 16a is driven by sending the shock wave generation timing signal to the pulser 21, the shock wave transducer 16a generates the shock waves to concentrate on the concretion 31 of the object such as the kidney in the living body P.

In the CFM processor 13, the ultrasonic wave doppler alteration frequency in the living body P is operated from the ultrasonic wave echo obtained by the transmit-receive controller 11, and the CFM process is carried out on the basis of the ultrasonic wave doppler alteration frequency. The resulting data of the CFM process is fed to the DSC 14, and the CFM image is stored in the FM 14a of the DSC 14. In the DSC 14, the CFM image is mixed with the monochrome B-mode section image, and the monochrome B-mode section image and the CFM image overlapped thereon are displayed on the display 15.

The writing of the data of the B-mode section image and the CFM image into the FM memory 14a of the DSC 14 with respect to the shock wave generation operation is performed as follows.

That is, the delayed frame pulse DFP is fed from the RPC 10 to the DSC 14 at the timing delayed by the predetermined period of time after the timing of the shock wave generation. The DSC 14 is started to store the data into the FM 14a at the timing of input of the delayed frame pulse DFP, and, when one frame of the data is stored in the FM 14a, the storing of the data is stopped. This step is repeated for every input of the delayed frame pulse DFP into the DSC 14 or every shock wave generation in the shock wave transducer 16a. The data writing timing by the delayed frame pulse DFP or the delayed pulse DP can be freely determined by the delay timing set 18, as described above. That is, in this embodiment, the reproducing and displaying of the still picture images such as the B-mode section image and the CFM image can be carried out at the best timing so that the best mode of the shock wave concentration positioning, the shock wave generation results and the disintegration state of the concretion or the like can be readily determined or adjusted and observed.

The CFM image display is effected as follows.

Different colors such as red and blue signify the approaching and going away of the concretion and surrounding tissue thereof to or from the ultrasonic wave probe 17, and the average speed or power of the moving concretion and surrounding tissue are signified by varying the display brightness. Since the concretion and surrounding tissue thereof are different in acoustic impedance, the concretion is moved more than the tissue thereby making it is easy to discriminate the moving concretion from the moving tissue in the CFM image 15b.

In this case, it is considered that the doppler signal of the concretion is larger with respect to that of the other tissue, particularly, the surrounding tissue, and hence the position of the concretion can be readily confirmed in the CFM image 15b by generating relatively weak shock waves during the positioning of the concretion. Also, even when the strong shock waves are generated in order to disintegrate the concretion after the positioning of the concretion, the concretion is moved more than the tissue because of the acoustic impedance difference, and hence the position of the concretion can be easily confirmed in the CFM image 15b.

Also, when the strong shock waves are imparted to the tissue of the living body P the tissue is deformed and moved, and this appears in the CFM image 15b. Hence, the concentration region or point where the shock waves are actually generated can be easily confirmed in the CFM image 15b.

Further, since the moving condition of the concretion against the shock waves is different, it is readily known whether the concretion is disintegrated or not. When the concretion is disintegrated, the sizes, moving directions and degree of dispersion of the disintegrated concretion pieces can be readily confirmed in the CFM image 15b by the extent of color mixture and the hue variation.

As described above, it is readily understood that by monitoring the B-mode section image and the CFM image overlapped thereon on the display during the shock wave treatment, the position of the object such as the concretion within the living body can be readily confirmed, and the position of the concentration point of the actual shock waves can be readily confirmed on the display. Hence, the positioning of the concentration point of the actual shock waves on the object can be readily performed. Also, the shock wave generation results of the object and extent and state of the disintegrated pieces of the object can be readily confirmed on the display. Therefore, the time and accuracy of the positioning of the concretion and the positioning of the shock waves on the concretion can be largely improved, and ineffective operations and operator's burden can be largely reduced.

In FIG. 6, there is shown a second embodiment of a shock wave treatment apparatus according to the present invention, having a similar structure to the first embodiment shown in FIG. 2, except an M-mode processor 22 for obtaining an M-mode image is also included.

Figure 7:
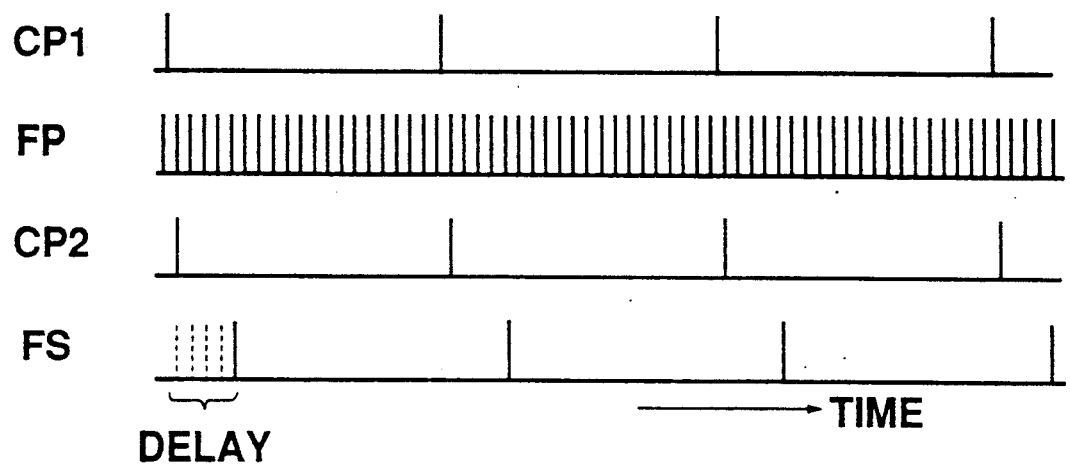
FIG. 7 is a timing chart including pulses representing action timings in the apparatus shown in FIG. 6.

In this embodiment, a first clock pulse generator 20a outputs a first clock pulse CP1 to a second clock pulse generator 20b. An RPG (rate pulse generator) 10 outputs a rate pulse as a frame pulse FP to a transmit-receive controller 11, a DSC (digital scan converter) 14 and the second clock pulse generator 20b. The second clock pulse generator 20b outputs a second clock pulse CP2 having the same interval as that of the first clock pulse CP1 as a shock wave generation timing signal to a delay counter 19 and a pulser 21 in synchronization with the frame pulse FP output from the RPG 10. The delay counter 19 outputs a freeze signal FS at a timing delayed by a certain period of time after the shock wave generation timing in sychronization with the frame pulse FP. In FIG. 7, there are schematically shown the first clock pulse CP1, the frame pulse FP, the second clock pulse CP2 and the freeze signal FS. The delay timing of the freeze signal FS output from the delay counter 19 is controlled to determine to integral number times as much as the interval of the frame pulse FP by a delay timing set 18.

Figure 10:
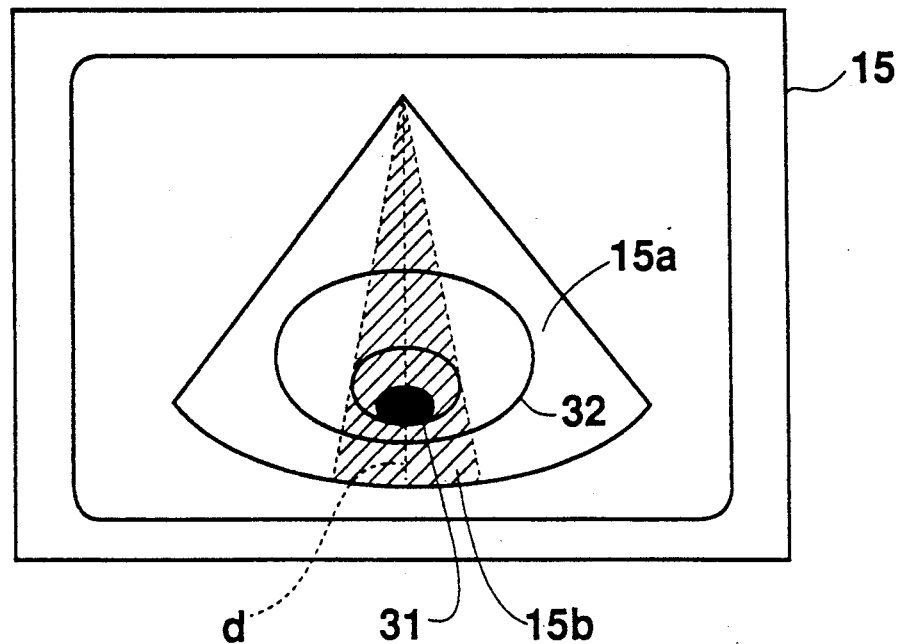
FIGS. 10(a)-(b) are schematic view showing a B-mode section image and an M-mode image on a display obtained in the embodiments shown in FIGS. 6 and 8.
Figure 10:
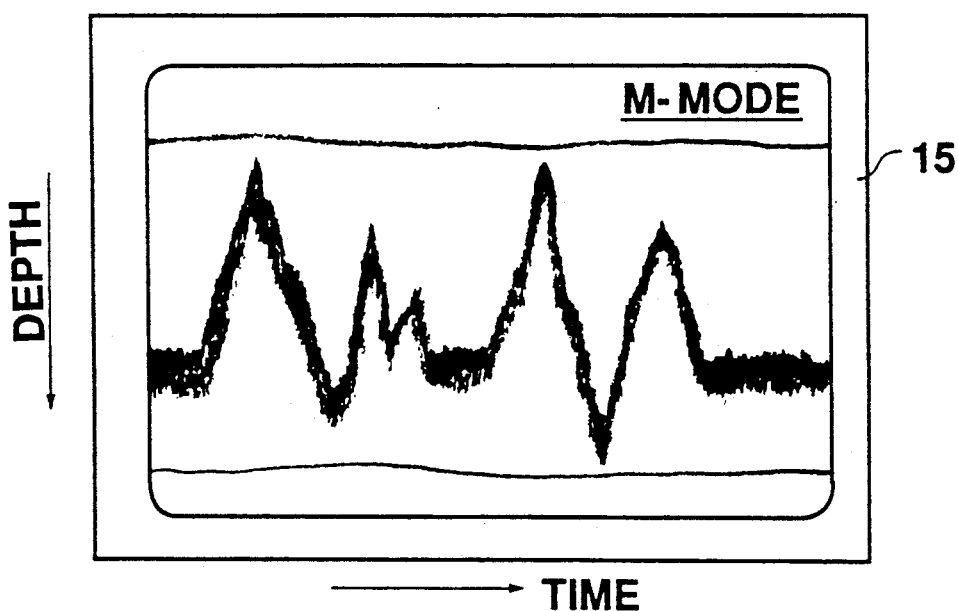

The M-mode processor 22 includes a detector for performing an amplitude detection of an output addition signal of the transmit-receive controller 11, and an A/D (analog-digital) converter for converting the amplitude detected signal to a digital detected signal to obtain a monochrome M-mode image. The operated results of the M-mode processor 22 are sent to the DSC 14. In this case, a CFM processor 13 performs the CFM process in both the B-mode and M-mode imagings. The CFM processor 13 can discriminate between the B-mode and M-mode image signals and mix or overlap the monochrome B-mode or M-mode image signals and the CFM signals to obtain the B-mode and M-mode images, as shown in FIG. 10.

In the M-mode imaging process, doppler signals are picked up from the ultrasonic wave echo and are processed with respect to only a certain direction such as, in practice, a shock wave concentration point direction d, as shown in FIG. 10a, in a depth of the living body P to obtain the M-mode image. One example of the M-mode image is shown in FIG. 10b. In this embodiment, in addition to the B-mode section image and the CFM image, the M-mode image can be utilized.

In case of the CFM imaging, the doppler signals are processed over a certain area to display the CFM image on the display. Hence, the reproduccable number of the frame images per second is approximately 10, which may be somewhat varied depending on the various conditions. In case of the M-mode imaging, the doppler signals are operated only along one direction such as, in practice, the direction the shock wave concentration point is positioned, and thus a much greater number of the frame images can be reproduced compared with that of the CFM imaging, that is, the resolving power per unit time can be largely improved, resulting in that the doppler signals can be observed with a high resolving power in the M-mode image.

In this embodiment, the writing of the data obtained in the B-mode processor 12, the CFM processor 13 and the M-mode processor 22 into the frame memory 14a of the DSC 14 with respect to the timing of the shock wave generation operation is carried out at the desired timing by using the freeze signal FS output from the delay counter 19 in a similar manner to the first embodiment described above. Hence, in this case, the reproducing and displaying of the still picture images can be carried out at the best timing so that the best mode of the shock wave concentration positioning, the shock wave generation results and the disintegration state of the concretion or the like can be readily determined or adjusted and observed. In this embodiment, the same effects and advantages as those of the first embodiment can be obtained.

In FIG. 8, there is shown a third embodiment of a shock wave treatment apparatus according to the present invention, having a similar structure to the first and the second embodiments described above.

In this embodiment, a timing controller 20 outputs a clock pulse CP as a shock wave generation timing signal to a delay counter 19 and a pulser 21. A delay counter 19 outputs a delayed clock pulse DCP to an RPG 10 at a timing delayed by a certain period of time after a shock wave generation timing. The delay timing of the delayed clock pulse DCP output by the delay counter 19 is continuously controlled by a delay timing set 18.

Figure 9:
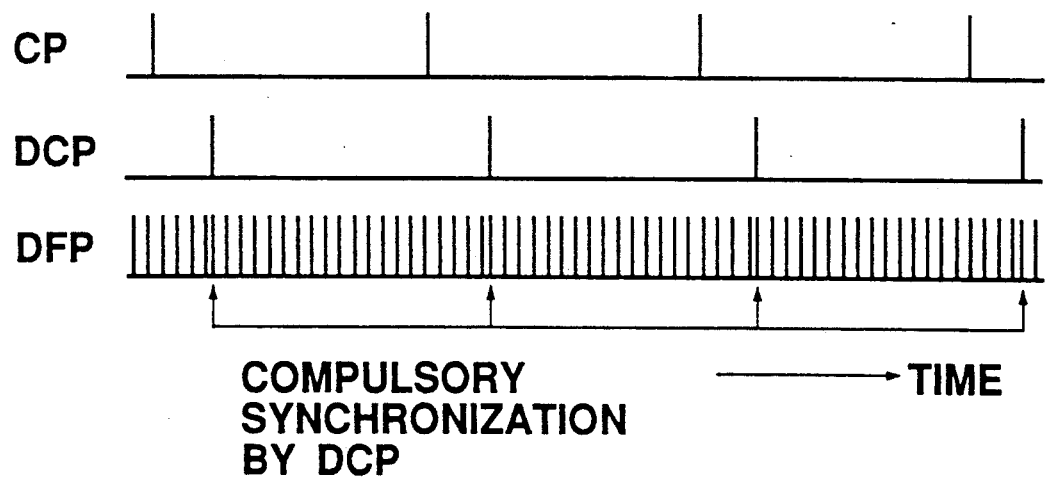
FIG. 9 is a timing chart including pulses representing action timings in the apparatus shown in FIG. 8.

In this case, in the RPG 10, a timing of a delayed frame pulse DFP is controlled by the delayed clock pulse DCP fed from the delay counter 19 in order to compulsorily synchronize with the timing of the delayed clock pulse DCP. In FIG. 9, there are schematically shown the clock pulse CP as the shock wave generation timing signal, the delayed clock pulse DCP and the delayed frame pulse DFP. In this embodiment, the writing of the data obtained in the B-mode processor 12, the CFM processor 13 and the M-mode processor 22 into the frame memory 14a of the DSC 14 with respect to the timing of the shock wave generation operation is carried out at the desired timing by using the delayed frame pulse DFP output from the RPG 10 in a similar manner to the above described embodiments.

In this embodiment, the delay timing of the delayed clock pulse DCP can be continuously changed, and hence more accurate control can be performed as compared with the second embodiment described above. In this case, the same effects and advantages as those of the first and second embodiments can be obtained.

Figure 11:
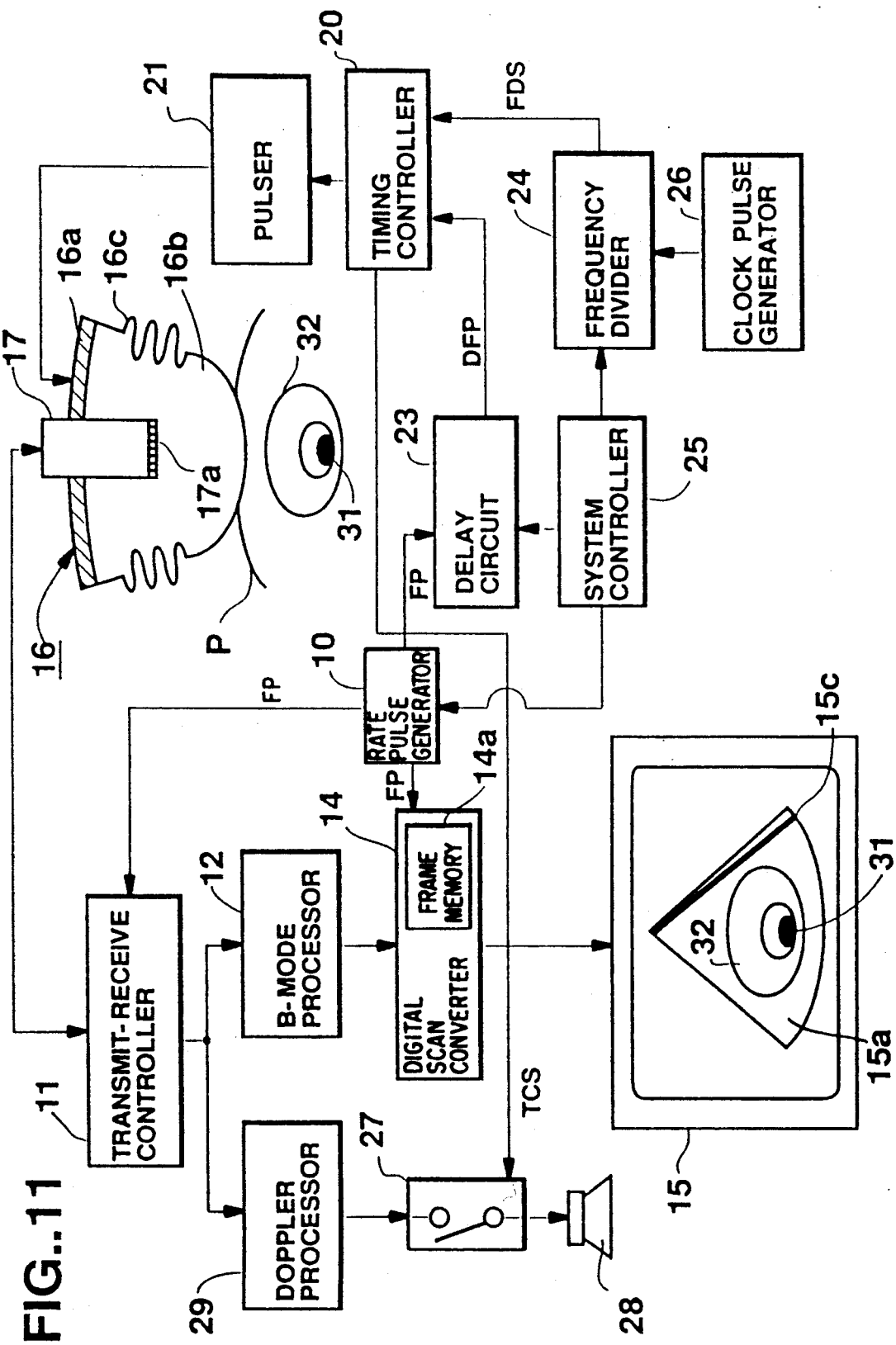
FIG. 11 is a block diagram of a fourth embodiment of a shock wave treatment apparatus according to the present invention.

In FIG. 11, there is shown a fourth embodiment of a shock wave treatment apparatus according to the present invention, having a similar construction to the first embodiment described above, except that a doppler processor 29 for outputting doppler information in an audio signal form is provided.

In this embodiment, a timing controller 20 outputs a timing control signal TCS as a shock wave generation timing signal to a pulser 21 and a switch 27 for performing an open-close control in synchronization with the timing control signal TCS. A clock pulse generator 26 generates a clock pulse to a frequency divider 24 which outputs a frequency divided signal FDS to the timing controller 20. An RPG (rate pulse generator) 10 generates a rate pulse as a frame pulse FP to a transmit-receive controller 11, a DSC (digital scan converter) 14 and a delay circuit 23. The delay circuit 23 sets back the frame pulse FP a certain period of time and sends a delayed frame pulse DFP to the timing controller 20.

Figure 12:
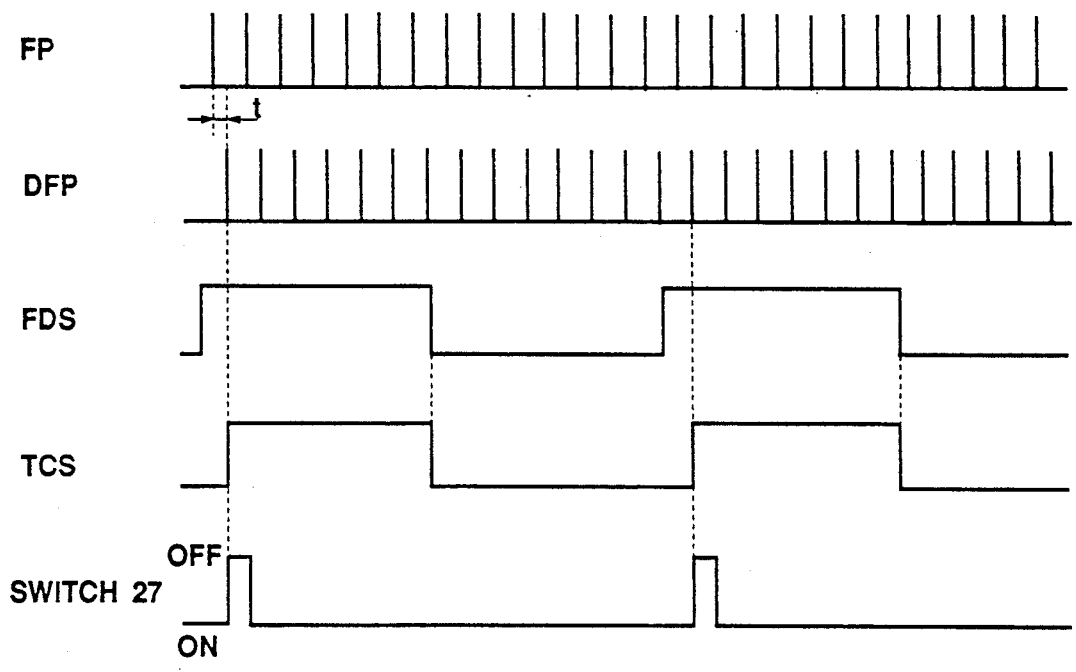
FIG. 12 is a timing chart including pulses representing action timings in the apparatus shown in FIG. 11.

In this case, the timing controller 20 outputs the shock wave generation timing signal TCS to the pulser 21 at a timing delayed by a desired period of time t after the timing of the frame pulse FP. Hence, the reproducing and displaying of the still picture images can be effected at the best timing in the same manner as described above. In FIG. 12, there are schematically shown the frame pulse FP, the delayed frame pulse DFP, the frequency divided signal FDS and the timing control signal TCS along with on and off modes of the switch 27. A system controller 25 controls the operation of the whole system of the shock wave treatment apparatus.

In the DSC, the writing of the data obtained in the B-mode processor 12 into a frame memory (FM) 14a with respect to the shock wave generation timing is started by the frame pulse FP fed from the RPG, and, when one frame of the data is stored in the FM 14a, the data storing is stopped. This step is repeated.

A doppler processor 29 includes a phase detector for effecting a phase detection of an ultrasonic wave echo sent from the transmit-receive controller 11, and a processor for setting a sample gate position. In the doppler processor 29, audio signals representing doppler information in the sample gate position is picked up from the ultrasonic wave echo. The audio signals are fed from the doppler processor 29 to a speaker 28 via the switch 27, and the speaker 28 reproduces doppler sounds from the audio signals. The doppler processor 29, the speaker 28 and the switch 27 may constitute first, second and third means, respectively.

The operation of this apparatus will now be described in detail in connection with FIGS. 11 and 12.

The delay circuit 23 outputs the delayed frame pulse DFP to the timing controller 20, and the frequency divider 24 sends the frequency divided signal FDS to the timing controller 20. After the frequency divided signal FDS is turned to the high level, the timing controller 20 outputs the timing control signal TCS as the shock wave generation timing signal at the timing of the following delayed frame pulse DFP, i.e., in synchronization with the leading edge of the delayed frame pulse DFP. The shock wave transducer 16a is driven to generate the shock waves at the timing of the leading edge of the shock wave generation timing signal TCS. By using this timing control, the affecting area direction or path of the shock waves in a B-mode section image can be freely controlled. For instance, that is, although it is not effective or practical for treating an object such as a concretion, by varying the delay time of the frame pulse FP in the delay circuit 23, the affecting area direction or path of the shock waves can be positioned in a right hand side end portion 15c in the B-mode section image 15a, as shown in FIG. 11.

When the ultrasonic wave echo is sent from the transmit-receive controller 11 to the doppler processor 29, the phase detection of the ultrasonic wave echo is effected and the doppler information is picked up in the form of the audio signals in the doppler processor 29. The audio signals are sent to the speaker 28 through the switch 27, and the speaker 28 reproduces the doppler sounds from the audio signals. By monitoring the doppler sounds, the extent and state of the shock wave generation and disintegrated object pieces and so forth can be readily confirmed.

In this embodiment, the doppler information pickup is carried out by using the pulsed wave doppler method, and the doppler information in the sample gate position determined in the B-mode section image is obtained. That is, by setting the sample gate position to a portion containing the disintegrated object pieces in advance, the doppler information of or near the disintegrated object pieces can be effectively obtained.

Figure 13:
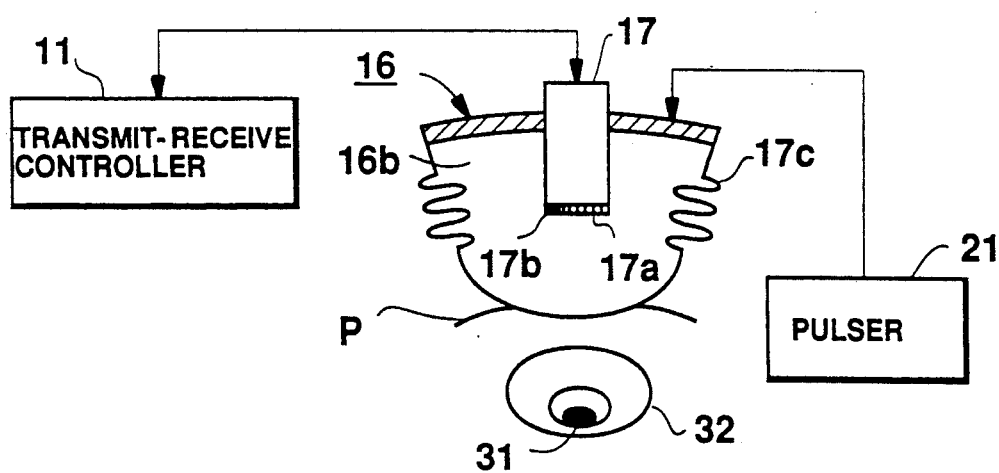
FIG. 13 is a fragmentary block diagram of a second embodiment of a ultrasonic wave probe used in a shock wave treatment apparatus according to the present invention.

Further, in this embodiment, the continuous wave doppler method may be also applied. In this case, a particular vibrator for the continuous wave doppler information pickup may be provided near the ultrasonic wave probe 17. Alternatively, a part 17b of the vibrator elements of the alloy 17a of the ultrasonic wave probe 17 may be used for the continuous wave doppler information pickup only, as shown in FIG. 13.

It is considered that, when the shock wave components are mixed with the doppler sounds to be output from the speaker 28, it becomes difficult to monitor the doppler sounds. In order to prevent this problem, the switch 27 is turned off in synchronization with the shock wave generation timing signal output from the timing controller 20 to remove the shock wave components from the doppler sounds. That is, as shown in FIG. 12, the switch 27 is turned off at the timing of the loading edge of the timing control signal TCS fed from the timing controller 20 to prevent the shock wave components from mixing in the doppler sounds, with the result of clearly monitoring the doppler sounds. Further, by making the OFF period of time of the switch 27 to be variable, more accurate or precise control for removing the shock wave component can be performed.

According to the present invention, a CFM processor 13 and/or an M-mode processor 22 of the second embodiment may be also provided in the apparatus described above, with the result of obtaining the same effects and advantages as those of the first and second embodiments.

Figure 14:
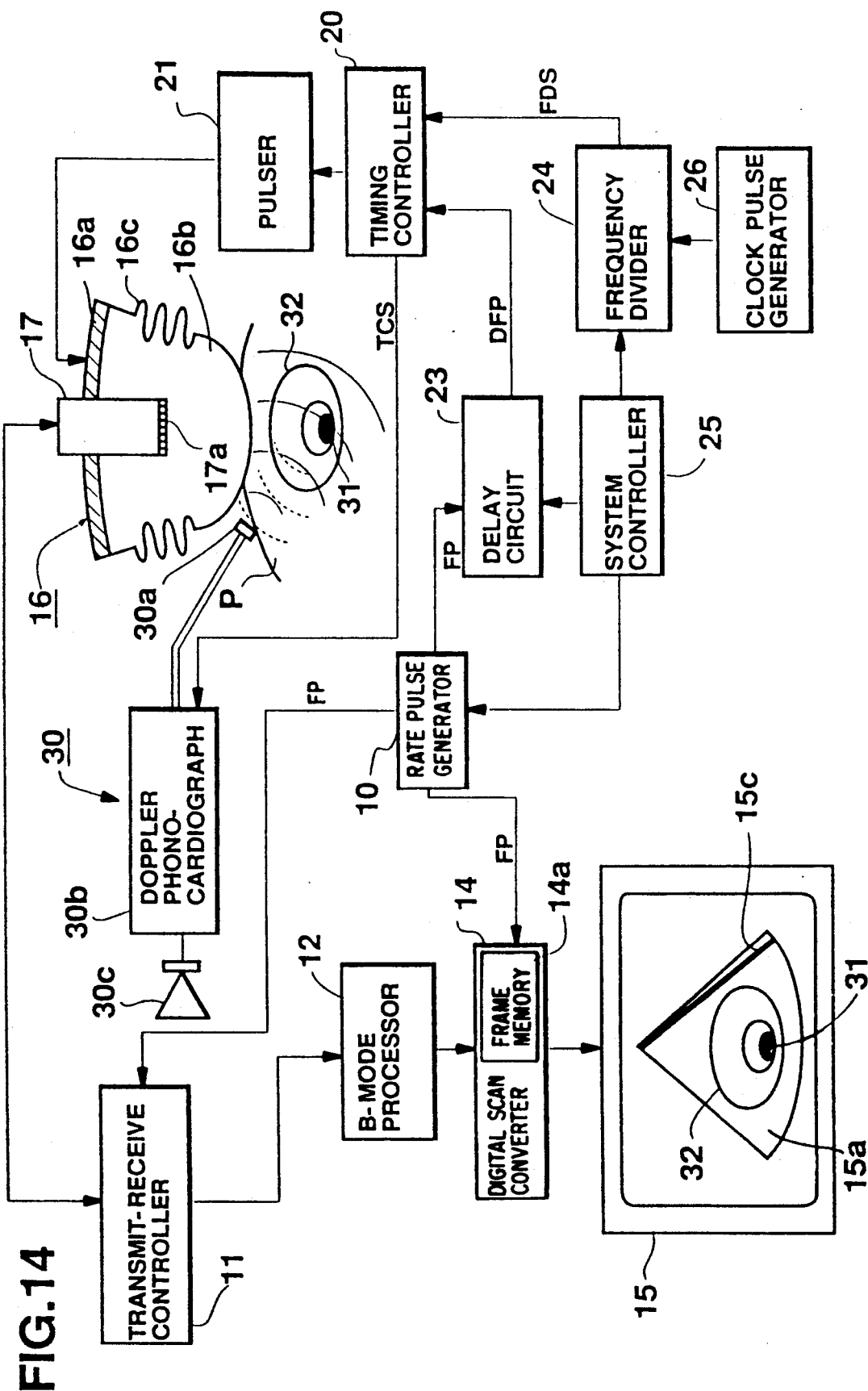
FIG. 14 is a block diagram of a fifth embodiment of a shock wave treatment apparatus according to the present invention.

In FIG. 14, there is shown a fifth embodiment of a shock wave treatment apparatus according to the present invention, having the same structure as the fourth embodiment shown in FIG. 11, except a doppler phonocardiograph 30 is provided.

In this case, the doppler phonocardiograph 30 includes a ultrasonic transmit-receive member 30a, a doppler phonocardiograph body 30b and a speaker 30c, which are coupled in series. The ultrasonic transmit-receive member 30a transmits a ultrasonic wave toward an object 31 such as a concretion within an internal organ such as a kidney 32 in a living body P and receives a reflected component. The body 30b picks up doppler information from the reflected component, and the doppler information is reproduced in the sound form by the speaker 30c. The body 30b and the speaker 30c may constitute first and second means, respectively.

In this embodiment, the body 30b includes a device for preventing shock wave components from mixing in the doppler sounds in synchronization with the shock wave generation timing signal output from the timing controller 20, this shock wave preventing device having a similar construction to that of the fourth embodiment shown in FIG. 11, with the result of clearly monitoring the doppler sounds. The body 30b may constitute third means. In this embodiment, the same effects and advantages as those of the fourth embodiment can be obtained.

Although the present invention has been described in its preferred embodiments with reference to the accompanying drawings, it is readily understood that the present invention is not restricted to the above described preferred embodiments, and various changes and modifications may be made in the present invention by those skilled in the art without departing from the spirit and scope of the present invention.

What is claimed is:

1. A shock wave treatment apparatus, comprising:
    means for generating a shock wave and transmitting the shock wave toward a living body having an object to be disintegrated by the shock wave;
    means for transmitting an ultrasonic wave toward the living body and for receiving an echo of the ultrasonic wave from the living body:
    means for generating a B-mode section image of the living body on the basis of the received ultrasonic wave echo;
    means for obtaining an ultrasonic wave doppler alteration frequency from the ultrasonic wave echo and for performing a color flow mapping process on the basis of the ultrasonic wave doppler alteration frequency to form a color flow mapping image of the living body;
    means for storing the color flow mapping image in synchronization with the generation and transmission of the shock wave; and
    means for displaying at least one of the B-mode section image and the color flow mapping image.

2. The apparatus of claim 1, further including means for forming an M-mode image of the living body on the basis of the ultrasonic wave echo, the display means displaying at least one of the B-mode section image, the color flow mapping image and the M-mode image.

3. The apparatus of claim 1, further including:
    means for performing a phase detection of the ultrasonic wave echo to obtain doppler information; and means for reproducing sound from the doppler information.

4. The apparatus of claim 1, further including:
means for generating a first signal to drive the shock wave generating means at a selected first time; and
means for generating a second signal to drive the B-mode section image generating means and the obtaining means at a selected second time, the selected second time being different from the selected first time.

5. The apparatus of claim 4, wherein the means for generating the first signal includes a timing controller and the means for generating the second signal includes a delay device and a delay timing controller for controlling the delay device, and wherein the first signal generated by the timing controller is supplied to the delay device at the selected first time and the delay device generates the second signal according to the delay timing controller at the selected second time, the selected second time occurring after the selected first time.

6. A shock wave treatment apparatus, comprising:
means for generating a shock wave and for transmitting the shock wave toward a living body having an object to be disintegrated by the shock wave;
means for transmitting an ultrasonic wave toward the living body and for receiving an echo of the ultrasonic wave reflected from the living body;
means for generating a B-mode section image of the living body on the basis of the received ultrasonic wave echo;
means for storing the B-mode section image in synchronization with the generation and transmission of the shock wave;
means for performing a phase detection of the ultrasonic wave echo to obtain doppler information;
means for reproducing sound from the doppler information; and
means for inhibiting a transmission of the doppler information from the means for performing a phase detection to the means for reproducing sound while the shock wave is transmitted toward the living body.

7. The apparatus of claim 6, further including
means for displaying the B-mode section image.

8. The apparatus of claim 7, further including means for obtaining an ultrasonic wave doppler alteration frequency from the ultrasonic wave echo and for performing a color flow mapping process on the basis of the ultrasonic wave doppler alteration frequency to form a color flow mapping image of the living body, the displaying means displaying at least one of the B-mode section image and the color flow mapping image.

9. The apparatus of claim 8, further including means for forming an M-mode image of the living body on the basis of the ultrasonic wave echo, the display means displaying at least one of the B-mode section image, the color flow mapping image and the M-mode image.

10. The apparatus of claim 6, wherein the means for performing a phase detection includes means for obtaining the doppler information by utilizing a pulsed wave doppler method.

11. The apparatus of claim 6, wherein the means for performing a phase detection includes means for obtaining the doppler information by utilizing a continuous wave doppler method.

12. The apparatus of claim 6, further including means for preventing a component of the shock wave from being reproduced in a sound form by the reproducing means.

* * * * *